US005741501A

United States Patent [19]

Justus et al.

[11] Patent Number: 5,741,501
[45] Date of Patent: Apr. 21, 1998

[54] PARA-HYDROXYPHENYLACETIC ACID FOR REDUCING THE REPELLENCY OF INSECTICIDES

[75] Inventors: Karl Justus, Köln; Jürgen Georg Lenz; Günther Nentwig, both of Leverkusen; Jürgen Scherkenbeck, Wermelskirchen; Martin Dambach, Burscheid; Gernot Wendler, Erftstadt, all of Germany

[73] Assignee: Bayer Aktiengesellschaft, Leverkusen, Germany

[21] Appl. No.: 690,286

[22] Filed: Jul. 26, 1996

[30] Foreign Application Priority Data

Aug. 2, 1995 [DE] Germany ............ 195 28 306.6

[51] Int. Cl.$^6$ ............ A01N 25/00; A01N 31/08
[52] U.S. Cl. ............ 424/405; 424/84; 424/403; 514/560; 514/570
[58] Field of Search ............ 424/84, 403, 405; 514/560, 570

[56] References Cited

U.S. PATENT DOCUMENTS 5,518,719 5/1996 Blum ............ 424/84

FOREIGN PATENT DOCUMENTS 588203 3/1994 European Pat. Off. .

OTHER PUBLICATIONS

J. Econ. Entomol. Bd. 76, Nr. 4, E.P. Wileyto, et al., pp. 752–756, "Attraction of the German Cockroach, *Blattella germanica* (Orthoptera Blatellidae), to Some Volatile Food Components" (1983).
Econ. Entomol. Michael K. Rust et al, Bd. 70, Nr. 1, pp. 34–38, "Using Pheromone Extract to Reduce Repellency of Blatticides" (1977).
Derwent Publications Ltd. Week 7538, Apr. 16, 1975, JP 50 042 053, Insect attraction . . . .
M. Gehret, Pest Control, pp. 56–58 (Jul. 1996).
M. Scharf, et al., Athropod Management Tests, 19, p. 402, (1994).
Abstract of U.S. 5,518,719 (1996).
Fuchs, et al., Z. ang. Ent., vol. 99, pp. 499–503, (1985).
R. Metzger, et al., Wissenschaftliche Zeitschrift, No. 1, pp. 79–85, (1980).
R. Metzger, et al., Wissenschaftliche Zeitschrift, No. 1, pp. 71–80, (1975).
M.K. Rust, et al., J. Econ. Entom., vol. 70, No. 1, pp. 34–38 (1977).

*Primary Examiner*—Neil S. Levy
*Attorney, Agent, or Firm*—Sprung Kramer Schaefer & Briscoe

[57] ABSTRACT

The present invention relates to the new use of p-hydroxyphenylacetic acid, by itself or in a mixture with other chemical compounds, for reducing the repellency of insecticides in the control of cockroaches, and to cockroach control compositions which comprise these mixtures, details being found in the description.

10 Claims, No Drawings

PARA-HYDROXYPHENYLACETIC ACID FOR REDUCING THE REPELLENCY OF INSECTICIDES

The present invention relates to the new use of para-hydroxyphenylacetic acid, by itself or in a mixture with other chemical compounds, for reducing the repellency of insecticides, inter alia in the control of cockroaches, and to cockroach control compositions which comprise para-hydroxyphenylacetic acid and mixtures of this carboxylic acid with other chemical compounds.

Cockroach infestation is a considerable hygiene problem in homes and businesses, which necessitates control of the cockroaches in many cases. However, because of their lifestyle, cockroaches are very, difficult to control. A particular problem here lies in the fact that many insecticides have repellent properties which reduce the success of the control.

M. K. Rust and D. A. Reierson (Journal of Economic Entomology 70 (1) (1977), 34–38) describe the use of cockroach faecal extract for improving the action of chlorpyrifos, propoxur, diazinon and Dri-die 67, and debate this effect as a reduction in the repellency of these insecticides.

A. E. Glaser (International Pest Control 22 (1) (1980), 7–8, 21) describes the same phenomenon for fenitrothion.

However, the method is unsuitable for commercial use, since only small amounts of anti-repellent substance can be provided for insecticides by extraction of cockroach faeces.

It has now been found, surprisingly, that the compound para-hydroxyphenylacetic acid of the following formula (I)

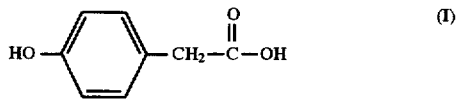

both by itself and in mixtures with other chemical compounds, reduces the repellency of insecticides in a similar manner to cockroach faecal extract, and can thus be employed particularly well in the control of cockroaches.

The anti-repellent p-hydroxyphenylacetic acid (p=para) according to the invention and mixtures thereof with other chemical compounds reduce the repellent action of insecticides, in particular pyrethroids, with respect to cockroaches and therefore increase the action of chemical insect control compositions.

The compound of the formula (I) is known and stable and, according to the invention, by itself and in mixtures with other chemical compounds, is highly active in chemical insect control compositions, preferably in bait and spray applications.

The compound of the formula (I) can be used either as the acid or in the form of its salts. It can also be used as a mixture of its lice acid with the particular salts.

Bases which can be used for preparation of the particular salts of phydroxyphenylacetic acid are all the bases customary in the chemistry of active compounds, preferably alkali metal, alkaline earth metal, ammonium, alkylammonium, dialkylammonium, trialkylammonium or tetraalkylammonium hydroxides, particularly preferably sodium, potassium, calcium or ammonium hydroxide, and especially preferably sodium hydroxide.

The compound of the formula (I) and/or its mixtures with other chemical compounds can be employed according to the invention in the control of cockroaches, that is to say insects of the order Blattariae, in particular of the family Blattellidae, preferably of the species *Blatella germanica*, or of the family Blattidae, preferably of the species *Blatta orientalis* and *Periplaneta americana*, and also against other species of cockroach, but especially preferably against *Blattella germanica*.

The compound of the formula (I) and/or its mixtures with other chemical compounds act according to the invention on the cockroaches such that the repellant action of insecticides, for example of pyrethroids, is reduced.

This effect occurs in all the mobile development stages (larvae, adults) of the cockroaches. Para-hydroxyphenylacetic acid and/or its mixtures with other chemical compounds can thus be employed quite generally in the control of cockroaches, regardless of the nature of the control method used. It can preferably be used in chemical control methods, and if appropriate together with other active agents, such as attracting bait materials or other attractants, synthetic or naturally occurring insecticides and the like.

From simple considerations or simple studies, it is easily possible for the expert to determine the mixtures and types of application and mounts favourable for the particular intended use.

p-Hydroxyphenylacetic acid and/or its mixtures with other chemical compounds is preferably applied in the customary sprays. The customary formulations which can be applied with the usually customary applicators can be used here. It is also possible to formulate the p-hydroxyphenylacetic acid and/or its mixtures with other chemical compounds into dusts or granules which can be scattered, if appropriate in a mixture with suitable insecticides. The amounts of p-hydroxyphenylacetic acid and/or its mixtures with other chemical compounds applied are preferably 0.1 to 500 mg per m$^2$, and particularly preferably 1 to 200 mg per m$^2$ (based on the p-hydroxyphenylacetic acid).

When used in a bait comprising insecticides, p-hydroxyphenylacetic acid and/or its mixtures with other chemical compounds is incorporated or is applied close to the bait material (for example on top). p-Hydroxyphenylacetic acid and/or its mixtures with other chemical compounds can also be in a form in which they are released over a relatively long period of time (slow-release formulations). For this, for example, they can be incorporated into polymeric material, paraffins, waxes and the like or be in microencapsulated form. The customary devices can serve as traps and the usual agents which attract feeding can serve as bait materials. Preferably, p-hydroxyphenylacetic acid and/or its mixtures with other chemical compounds are employed in amounts of 0.0001 to 100 mg (especially preferably 0.01 to 20 mg) per gram of bait (based on p-hydroxyphenylacetic acid).

The present invention also relates to cockroach control compositions which comprise, if appropriate in addition to customary carders and auxiliaries and/or other additives (such as baits or attractants), p-hydroxyphenylacetic acid and/or its mixtures with other chemical compounds and at least one insecticidally active substance, it being possible for the p-hydroxyphenylacetic acid and/or its mixtures with other chemical compounds to be mixed with the other constituents or to be present in a separate arrangement.

Other chemical compounds means, in particular, organic carboxylic acids, particularly preferably benzoic acid, phenylacetic acid, anthranilic acid, 3-(m-hydroxyphenyl) propionic acid, 3-(p-hydroxyphenyl)propionic acid, 2-hydroxypropionic acid, capric acid, palmitic acid, stearic acid, glutaric acid, adipic acid, pimelic acid, suberic acid, azelaic acid, methylpimelic acid, fumaric acid or maleic acid.

Insecticidal substances which can be used are all substances which are active against cockroaches, since no undesirable interaction occurs between the insecticidally acting substances and p-hydroxyphenylacetic acid or the mixtures according to the invention.

Insecticidally acting substances can belong to, for example, the insecticidally acting phosphoric acid esters, carbamates, naturally occurring pyrethrins and synthetic pyrethroids, amidinohydrazones, sulphuramides, nitroimino, nitromethylene, cyanoimino or cyanomethylene compounds, pyrrolidine-2,4-dione derivatives, pyrazoline derivatives, avermectin and ivermectin derivatives, azadirachtrines, annonines and/or ryanodines.

It is equally possible to use chitinsynthesis inhibitors (for example triflumeron, duflubenzuron, lufenuron, flufenoxuron and others), and also juvenile hormones and mimetics thereof (for example methoprene, hydroprene, fenoxycarb, pyriproxyfen and others) or "household agents" (borax, yeast, baking powder and others).

As insecticidal partners which are particularly preferred according to the invention for mixing with p-hydroxyphenylacetic acid and/or its mixtures with other chemical compounds there may be mentioned:

1) Carbamide Acid Ester of the Formula (II)

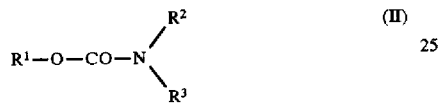

in which

R$^1$ represents an optionally substituted carbocyclic or heterocyclic aromatic radical, or represents an optionally substituted oxime radical, the radicals R$^1$ derailed below being preferred, R$^2$ represents C$_1$-C$_4$-alkyl and R$^3$ represents hydrogen or C$_1$-C$_4$-alkyl, or represents a radical U, wherein U represents the radical —CO—R$^4$, wherein R$^4$ represents halogen, C$_1$-C$_4$-alkyl, C$_1$-C$_4$-alkoxy, C$_3$-C$_5$-alkenoxy, C$_3$-C$_5$-alkinoxy, C$_1$-C$_4$-alkylthio, C$_1$-C$_4$-alkylamino, di-C$_1$-C$_4$-alkylamino or C$_1$-C$_4$-alkylhydroxylamino, or represents phenoxy, phenylthio or phenylamino which are optionally substituted by halogen, nitro, cyano, trifluoromethyl, C$_1$-C$_4$-alkyl, C$_1$-C$_4$-alkoxy, C$_1$-C$_4$-alkylenedioxy, C$_1$-C$_4$-alkylthio or C$_1$-C$_4$-alkoxy-carbonyl, or represents 2,3-dihydro-2,2-dimethyl-7-benzofuranyl or represents the radical of the formula

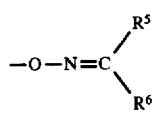

wherein

R$^5$ represents hydrogen, C$_1$-C$_4$-alkyl or di-C$_1$-C$_4$-alkylaminocarbonyl and R$^6$ represents C$_1$-C$_4$-alkyl, C$_1$-C$_4$-alkylthio, cyano-C$_1$-C$_4$-alkylthio or C$_1$-C$_4$-alkylthio-C$_1$-C$_4$-alkyl, or the two radicals R$^5$ and R$^6$ together represent C$_2$-C$_8$-alkanediyl which is optionally interrupted by oxygen, sulphur, SO or SO$_2$, or in which U represents the radical —S$_v$(O)$_w$—R$^7$, wherein v represents 1 or 2 and w represents 0, 1 or 2, where, in the case where v represents 2, w denotes 0, R$^7$ represents C$_1$-C$_4$-alkyl, C$_3$-C$_5$-alkenyl, C$_3$-C$_5$-alkinyl or C$_3$-C$_6$-cycloalkyl which are optionally substituted by halogen, or represents phenyl, benzyl or phenylethyl which are optionally substituted by halogen, cyano, nitro, trifluoromethyl, trifluoromethoxy, trifluoromethylthio, C$_1$-C$_4$-alkyl or C$_1$-C$_4$-alkoxy, or represents the radical of the formula

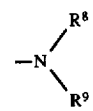

wherein

R$^8$ represents C$_1$-C$_4$-alkyl, C$_3$-C$_5$-alkenyl, C$_3$-C$_5$-alkinyl, C$_3$-C$_6$-cycloalkyl or benzyl and R$^9$ represents C$_1$-C$_4$-alkyl, C$_3$-C$_5$-alkenyl, C$_3$-C$_5$-alkinyl, C$_3$-C$_6$-cycloalkyl, benzyl, phenylethyl, halogenocarbonyl, formyl, C$_1$-C$_4$-alkylcarbonyl, C$_1$-C$_4$-alkoxycarbonyl, C$_1$-C$_4$-alkoxyphenoxycarbonyl, C$_3$-C$_5$-alkinoxycarbonyl, C$_3$-C$_5$-alkenoxycarbonyl, C$_1$-C$_4$-alkylthiocarbonyl, C$_1$-C$_4$-alkyl-amino-carbonyl, C$_1$-C$_4$-alkyl-hydroxylamino-carbonyl, C$_1$-C$_{10}$-alkylphenoxycarbonyl, di-C$_1$-C$_4$-alkylaminocarbonyl, phenylthiocarbonyl, phenoxycarbonyl or 2,3-dihydro-2,2-dimethyl-7-benzofuranyloxycarbonyl, or represents phenylsulphenyl, phenylsulphinyl, phenylsulphonyl or phenyl which are optionally substituted by halogen, cyano, nitro, trifluoromethyl, C$_1$-C$_{10}$-alkyl or C$_1$-C$_4$-alkoxy, or represents the radical of the formula

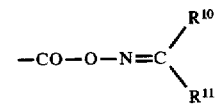

wherein

R$^{10}$ has the meaning given above for R$^5$ and

R$^{11}$ has the meaning given above for R$^6$, and wherein, furthermore, in the radial

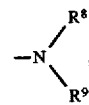

the radicals R$^8$ and R$^9$ together represent a hydrocarbon chain which has 3 to 8 carbon atoms and is optionally interrupted by oxygen or sulphur, and wherein R$^7$ furthermore can also represent the same radical to which the radical S$_v$(O)$_w$—R$^7$ is bonded.

Especially preferred active compound components are carbamic acid esters of the formula II in which R$^1$ represents radicals from the series consisting of phenyl, naphthyl, 2,3-dihydro-7-benzofuranyl, pyrazolyl or pyrimidinyl which are optionally substituted by C$_1$-C$_4$-alkyl, C$_2$-C$_4$-alkenyl, C$_1$-C$_4$-alkoxy, C$_1$-C$_4$-alkoxymethyl, C$_1$-C$_4$-alkylthio, C$_1$-C$_4$-alkylthiomethyl, C$_1$-C$_4$-alkylamino, di-(C$_1$-C$_4$-alkyl)-amino, di-(C$_3$-C$_4$-alkenyl)-amino, halogen, dioxolanyl, methylenedioxy and/or by the radical —N=CH—N(CH$_3$)$_2$, or in which $R^1$ represents an alkylideneamino radical of the formula

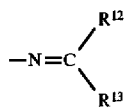

in which $R^{12}$ and $R^{13}$ have the meaning given above for $R^5$ and $R^6$ respectively, $R^2$ represents $C_1-C_4$-alkyl and $R^3$ represents hydrogen or $C_{1-C4}$-alkcyl (preferably hydrogen).

Examples which may be mentioned of the carbamic acid esters of the formula (II) are the following N-methylcarbamic acid esters: 2-methyl-phenyl, 2-ethyl-phenyl, 2-iso-propyl-phenyl, 2-sec-butyl-phenyl, 2-methoxy-phenyl, 2-ethoxy-phenyl, 2-iso-propoxy-phenyl, 4-methyl-phenyl, 4-ethyl-phenyl, 4-n-propyl-phenyl, 4-methoxy-phenyl, 4-ethoxy-phenyl, 4-n-propoxy-phenyl, 3,4,5-trimethyl-phenyl, 3,5-dimethyl-4-methylthio-phenyl, 3-methyl-4-dimethylaminophenyl, 2-ethylthiomethyl-phenyl, 1-naphthyl, 2,3-dihydro-2,2-dimethyl-7-benzofuranyl, 2,3-(dimethylmethylenedioxy)-phenyl, 2-(4,5-dimethyl-1,3-dioxolan-1-yl)-phenyl, 1-methylthio-ethylideneamino, 2-methylthio-2-methylpropylideneamino, 1-(2-cyano-ethylthio)-ethylideneamino and 1-methylthiomethyl-2,2-dimethylpropylideneamino N-methyl carbamate, 2-iso-propoxy-phenyl N-methyl carbamate being preferred.

2) Carboxylic Acid Esters of the Formula (III)

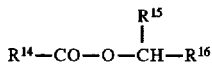

in which $R^{14}$ represents an open-chain or cyclic alkyl radical which is optionally substituted by halogen, alkyl or cycloalkyl, or by alkenyl which is optionally substituted by halogen, alkyl and/or alkoxy, or by phenyl or styryl which are optionally substituted by halogen or optionally halogen-substituted radicals from the series consisting of alkyl, alkoxy, alkylenedioxy and/or alkylthio, or by spirocyclically linked, optionally halogen-substituted cycloalk(en)yl, which is optionally benzo-fused, and in which, furthermore, $R^{15}$ represents hydrogen, alkyl, halogenoalkyl, alkenyl, alkinyl or cyano and $R^{16}$ represents an optionally substituted alkyl or aryl radical or represents a heterocyclic radical, or, together with $R^{15}$ and the carbon atom to which the two radicals are bonded, forms a cyclopentanone ring.

Especially preferred active compound components are carboxylic acid esters of the formula (III) in which (a) $R^4$ represents the radical

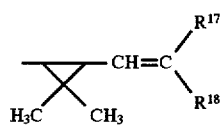

wherein $R^{17}$ represents hydrogen, methyl, fluorine, chlorine or bromine and $R^{18}$ represents methyl, fluorine, chlorine, bromine, $C_1-C_2$-fluoroalkyl or $C_1-C_2$-chlorofluoroalkyl, or represents phenyl which is optionally substituted by halogen and/or optionally halogen-substituted radicals from the series consisting of $C_1-C_4$-alkyl, $C_1-C_4$-alkoxy, $C_1-C_4$-alkylthio and/or $C_1-C_2$-alkylenedioxy, or wherein the two radicals $R^7$ and $R^8$ represent $C_2-C_5$-alkanediyl (alkylene);

or in which b) $R^{14}$ represents the radical

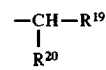

wherein $R^{19}$ represents phenyl which is optionally substituted by halogen and/or by optionally halogen-substituted radicals from the series consisting of $C_1-C_4$-alkyl, $C_1-C_4$-alkoxy, $C_1-C_4$-alkylthio or $C_1-C_2$-alkylenedioxy and $R^{20}$ represents isopropyl or cyclopropyl;

or in which (c) $R^{14}$ represents methyl or one of the radicals

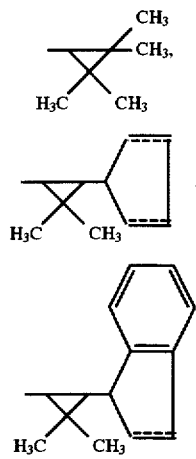

wherein the dotted lines are intended to indicate possible double bonds, and in which $R^{14}$ represents hydrogen, $C_1-C_4$-alkyl, $C_1-C_4$-halogenoalkyl, cyano or ethinyl and $R^{16}$ represents the radicals of the series consisting of phenyl, furyl and tetrahydrophthalimido, where these radicals can be substituted by halogen and/or radicals from the series consisting of $C_1-C_4$-alkyl, $C_2-C_4$-alkenyl, $C_1-C_4$-alkoxy, $C_2-C_4$-alkenoxy, $C_1-C_4$-alkylthio, $C_1-C_2$-alkylenedioxy, phenoxy and/or benzyl, which in their turn can be substituted by halogen, and wherein $R^6$ preferably represents tetrafluorophenyl, 3,4-dichlorophenyl or tetrahydrophthalimido, or represents phenoxy-phenyl which can be substituted by halogen (preferably fluorine) in one or both phenyl ring.

The naturally occurring pyrethroids (such as pyrethrum) or synthetic pyrethroids are furthermore particularly preferred carboxylic acid esters of the formula (III).

Examples which may be mentioned of carboxylic acid esters of the formula (III) which are particularly preferred according to the invention are 3,4,5,6-tetrahydro-phthalimido-methyl 2,2-dimethyl-3-(2-methyl-propen-1-yl)-cyclopropane-carboxylate, 3-phenoxy-benzyl 2,2-dimethyl-3-(2,2-dichloro-vinyl) cyclopropane-carboxylate, α-cyano-3-phenoxy-benzyl 2,2-dimethyl-3-(2,2-dichlorovinyl)-cyclopropane-carboxylate, α-cyano-4-fluoro-3-phenoxy-benzyl 2,2-dimethyl-3-(2,2-dichlorovinyl)-cyclopropane-carboxylate, 2,3,5,6-tetrafluoro-benzyl 2,2-dimethyl-3-(2,2-dichlorovinyl)-cyclopropane-carboxylate, α-cyano-3-phenoxy-benzyl 2,2-dimethyl-3-(2,2-dibromovinyl)-cyclopropane-carboxylate and α-cyano-3-phenoxy-benzyl 3-methyl-2-(4-chloro-phenyl)-butanoate.

3) Phosphoric Acid Esters and Phosphonic Acid Esters of the General Formula (IV)

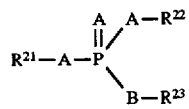

in which

A is identical or different and represents O or S and

B represents O, S or —NH—, or represents a direct bond between the central P atom and $R^{23}$ and $R^{21}$ and $R^{22}$ are identical or different and represent optionally substituted alkyl or aryl and, $R^{23}$ represents hydrogen, optionally substituted alkyl, aryl, heteroaryl, aralkyl, alkenyl or dioxanyl or an oxime radial, or represents the same radical to which it is bonded.

Particularly preferred phosphoric acid esters and phosphonic acid esters of the formula (IV) are those in which $R^{21}$ and $R^{22}$ are identical or different and represent $C_1$–$C_4$-alkyl or phenyl, $R^{23}$ represents hydrogen, or represents alkyl having 1 to 4 carbon atoms, which is optionally substituted by halogen, hydroxyl, cyano, optionally halogen-substituted phenyl, carbamoyl, alkylsulphonyl, alkylsulphinyl, alkylcarbonyl, alkoxy, alkylthio, alkoxycarbonyl or alkylaminocarbonyl, the latter having in each case up to 6 carbon atoms, $R^{23}$ furthermore represents alkenyl having up to 4 carbon atoms, which is optionally substituted by halogen-substituted phenyl or $C_1$–$C_4$-alkoxycarbonyl, or $R^{23}$ represents the radical of the general formula

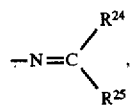

wherein $R^{24}$ and $R^{25}$ have the meaning given above for $R^5$ and $R^6$ respectively, or represent cyano or phenyl, $R^{23}$ furthermore represents dioxanyl, which is substituted by the same radical to which $R^{22}$ is bonded, or $R^{23}$ represents the same radical to which it is bonded, or $R^{23}$ represents phenyl, which is optionally substituted by methyl, nitro, cyano, halogen and/or methylthio, and wherein $R^{23}$ moreover particularly preferably represents heteroaromatic radicals, such as pyridinyl, quinolinyl, quinoxalinyl, pyrimidinyl or benzo-1,2,4-triazinyl, which are optionally substituted by $C_1$–$C_4$-alkoxy, $C_1$–$C_4$-alkylthiomethyl, $C_1$–$C_4$-alkyl and/or by halogen.

The following may be mentioned specifically:

O,O-dimethyl- and O,O-diethyl-O-(2,2-dichloro- and 2,2-dibromovinyl)-phosphoric acid ester, O,O-diethyl-O-(4-nitro-phenyl)-thionophosphoric acid ester, O,O-dimethyl-O-(3-methyl-4-methylthio-phenyl)-thionophosphoric acid ester, O,O-dimethyl-O-(3-methyl-4-nitro-phenyl)-thionophosphoric acid ester, O-ethyl-S-n-propyl-O-(2,4-dichlorophenyl)-thionophosphoric acid ester, O,O-ethyl-S-n-propyl-O-(4-methylthio-phenyl)-thionophosphoric acid ester, O,O-dimethyl-S-(4-oxo-1,2,3-benzotriazin-3-yl-methyl)-thionophosphoric acid ester, O-methyl-O-(2-iso-propyl-6-methoxy-pyrimidin4-yl)-thionomethanephosphonic acid ester, O,O-diethyl-O-(2-iso-propyl-6-methyl-pyrimidin-4-yl)-thionophosphoric acid ester, O,O-diethyl-O-(3-chloro-4-methyl-coumarin-7-yl)-thionophosphoric acid ester, O,O-dimethyl-2,2,2-trichloro-1-hydroxy-ethane-phosphonic acid ester, O,O-dimethyl-S-(methylaminocarbonyl-methyl)-thionophosphonic acid ester, O-methyl-O-(6-methoxy-2-tert-butyl-pyrimidin-4-yl)-thionoethanephosphonic acid diester.

4) Nitromethylene, Nitroimino, Cyanoimino or Cyanomethylene Derivatives of the Formula (V)

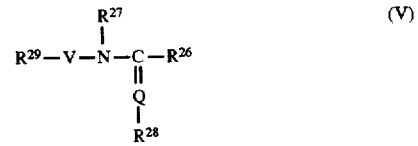

in which $R^{26}$ represents $C_1$–$C_4$-alkyl (preferably methyl or ethyl), or represents the group

in which $R^{30}$ denotes $C_1$–$C_4$-alkyl (preferably methyl or ethyl), or $R^{30}$ together with $R^{27}$ represents an optionally branched $C_2$–$C_5$-alkanediyl chain (preferably —$(CH_2)_2$— or —$(CH_2)_3$—), and $R^{31}$ denotes hydrogen or $C_1$–$C_4$-alkyl (preferably hydrogen).

$R^{27}$ represents $C_1$–$C_4$-alkyl (preferably methyl or ethyl), or together with $R^{30}$ represents an optionally branched $C_2$–$C_5$-alkanediyl chain (preferably —$(CH_2)_2$— or —$(CH_2)_3$—).

$R^{28}$ represents $NO_2$ or CN, $R^{29}$ represents an optionally substituted (preferably substituted by halogen and/or $C_1$–$C_4$-alkyl) heteroaromatic radical (preferably a pyridyl radical) (where $R^{29}$ particularly preferably represents the 2-chloropyrid-5-yl group), Q represents =C— or =N— and V represents a direct bond, or represents a $C_1$–$C_3$-alkanediyl radical (preferably —$CH_2$—).

Some particularly preferred compounds of the formula (V) are listed specifically below by way of example:

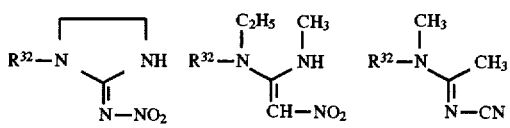

wherein $R^{32}$ denotes the

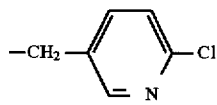

radical

In the abovementioned general formulae and definitions of radicals, the radicals have the following general and preferred meaning:

Alkyl as such or as a constituent of alkoxy or alkoxycarbonyl denotes straight-chain or branched alkyl having 1 to 5, preferably 1 to 4 and particularly preferably 1 to 3, carbon atoms, where methyl, ethyl, n- and i-propyl and n-, i-, s- and t-butyl may be mentioned specifically and where methyl and ethyl, in particular methyl, are to be particularly singled out.

In optionally substituted phenyl, phenoxy or phenoxycarbonyl, the phenyl ring preferably carries one to three, particularly preferably one or two, substituents, which can be identical or different. Substituents can be all the substituents customary in the chemistry of active compounds. Preferred substituents which may be mentioned are: $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, nitro, hydroxy and halogen (preferably fluorine, chlorine and/or bromine).

Depending on their particular physical and/or chemical properties, the p-hydroxyphenylacetic acid and/or its mixtures with other chemical compounds and/or the insecticidal substances and the mixtures of p-hydroxyphenylacetic acid and/or its mixtures with other chemical compounds with the insecticidal substances can be converted to the customary formulations, such as solutions, emulsions, suspensions, powders, foams, pastes, granules, aerosols, natural and synthetic materials impregnated with active compound and very fine capsules in polymeric substances.

These formulations are produced in a known manner, for example by mixing the active compounds with auxiliaries and/or extenders, that is liquid solvents and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; as solid carriers there are suitable: for example ground natural minerals, such as kaolins, clays, talc, chalk quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or fog-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

In the case of bait formulations (preferably scattered bait formulations or solid bait formulations), the formulations can additionally comprise other additives which attract cockroaches and/or cause them to ingest the insecticidal substances. Attractants and feeding substances which can be used are all the preparations customarily used, such as naturally occurring or synthetic odiferous substances and/or substances which are readily ingested by cockroaches, such as cereal- or sugar-based products containing starch, protein and/or sugar.

The formulations preferably comprise 0.001 to 95, in particular 0.01 to 70 percent by weight of p-hydroxyphenylacetic acid and/or its mixtures with other chemical compounds.

The formulations preferably comprise (if appropriate in addition to p-hydroxyphenylacetic acid and/or its mixtures with other chemical compounds) between 0.1 and 95, in particular 0.5 and 90 percent by weight of insecticidal substances.

The cockroach control compositions are used in a customary manner appropriate for the use form.

The biological activity of p-hydroxyphenylacetic acid and/or its mixtures with other chemical compounds is illustrated with the aid of the following examples.

EXAMPLE A

Improvement in a Bait Action

In a room (2.25×4.70 m) are in 2 opposite corners in each case a hiding place and in each case a drink, and in the other corners in each case a piece of rusk. One day after release of 20 male and 20 female cockroaches (*Blattella germanica*), in each case a bait can with an insecticide-containing bait for ingestion (insecticidal active compound: 0.5% by weight of ethylchlorpyrifos) is placed at a 40 cm wall distance from the rusk.

This bait either comprises p-hydroxyphenylacetic acid or is untreated.

3 rooms are in each case occupied by treated bait cans and 3 with untreated bait cans.

The mortality of the male and female animals is determined on the following 3 days.

Test result:

| Type of treatment | % Mortality rate | | |
|---|---|---|---|
| | 1 day | 2 days | 3 days |
| Control (only insecticide) | 22 | 42 | 52 |
| Insecticide + 10 mg of p-hydroxyphenylacetic acid | 46 | 58 | 63 |

EXAMPLE B

Improvement in the Action of a Spray in a Laboratory Test

Ceramic tiles are sprayed with an aqueous spray liquor which comprises (a) the insecticidal active compound cyfluthrin or (b) cyfluthrin and p-hydroxyphenylacetic acid, so that the amount of cyfluthrin applied is 20 mg of active compound per m$^2$ and the amount of p-hydroxyphenylacetic acid applied is 1 mg per m$^2$.

In each case one of these tiles is placed in the corner of a container (49×59 cm, height 29.5 cm) which contains a drink food, a hiding place and male and female *Blattella germanica* (5 of each) introduced 24 hours beforehand. Each experiment is repeated 5 times.
Test result:

| Type of treatment | % Mortality rate | |
|---|---|---|
| | 1 day | 2 days |
| Control (only insecticide) | 32 | 44 |
| Insecticide + p-hydroxyphenylacetic acid | 68 | 78 |

EXAMPLE C

Improvement in the Action of a Spray in a Test in Practice

An aqueous spray liquor which comprised (a) the insecticidal active compound β-cyfluthrin or (b) β-cyfluthrin and p-hydroxyphenylacetic acid was used in Australia, so that the amount of β-cyfluthrin applied is 6.25 mg of active compound per m$^2$ (half the recommended amount) and the amount of p-hydroxyphenylacetic acid applied is 1 mg per m$^2$.

The experiments were carried out in flats with extremely difficult hygiene conditions. 7 to 8 units were treated per preparation (β-cyfluthrin or β-cyfluthrin and p-hydroxyphenylacetic acid). The activity was determined by evaluation of adhesive trap catches before and at certain times after the treatment.
Test result:

| Type of treatment | % Reduction after 7 days |
|---|---|
| Control (only insecticide) | 37 |
| Insecticide + p-hydroxyphenylacetic acid | 65 |

It will be understood that the specification and examples are illustrative but not limitative of the present invention and that other embodiments within the spirit and scope of the invention will suggest themselves to those skilled in the art.

We claim:

1. A method of reducing the repellency of an insecticide applied to a surface which comprises applying to such surface a cockroach insecticide and a repellency-reducing effective amount of para-hydroxyphenylacetic acid or a salt thereof.

2. A method according to claim 1, wherein the para-hydroxyphenylacetic acid is admixed with at least one other compound for reducing the repellency of the insecticide.

3. A method according to claim 1, wherein the para-hydroxyphenylacetic acid or a salt thereof is mixed with at least one auxiliary, extender or surface active agent.

4. The method according to claim 1 wherein the insecticide is an insecticide for killing cockroaches and the insecticide and the para-hydroxyphenylacetic acid or a salt thereof is applied to the cockroaches or to an environment where they reside.

5. A method of combatting cockroach infestation which comprises applying to said cockroach or to an environment where said cockroach reside an effective amount of a composition which comprises para-hydroxyphenylacetic acid and an insecticide for cockroach control.

6. The method according to claim 5, wherein the insecticide is a carbamide acid ester, a carboxylic acid ester, a phosphoric acid ester, or a nitromethylene, nitroimino, cyanoimino or a cyanomethylene compound.

7. The method according to claim 6, wherein the insecticide is cyfluthrin, β-cyfluthrin, ethylchlorpyrifus,

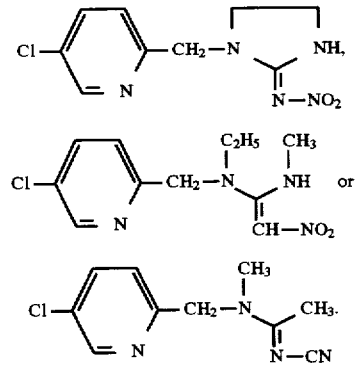

8. The method according to claim 6, wherein the insecticide is a carboxylic acid ester selected from the group consisting of
3,4,5,6-tetrahydro-phthalimido-methyl 2,2-dimethyl-3-(2-methyl-propen-1-yl)-cyclopropane-carboxylate, 3-phenoxy-benzyl 2,2-dimethyl-3-(2,2-dichloro-vinyl) cyclopropane-carboxylate,α-cyano-3-phenoxybenzyl2,2-dimethyl-3-(2,2-dichlorovinyl)-cyclopropane-carboxylate, α-cyano-4-fluoro-3-phenoxy-benzyl 2,2-dimethyl-3-(2,2-dichlorovinyl)-cyclopropane-carboxylate, 2,3,5,6-tetrafluoro-benzyl 2,2-dimethyl-3-(2,2-dichlorovinyl)-cyclopropane-carboxylate, α-cyano-3-phenoxy-benzyl 2,2-dimethyl-3-(2,2-dibromovinyl)-cyclopropane-carboxylate and α-cyano-3-phenoxy-benzyl 3-methyl-2-(4-chlorophenyl)-butanoate.

9. The method according to claim 6, wherein the insecticide is a phosphoric acid ester selected from the group consisting of O,O-dimethyl- and O,O-diethyl-O-(2,2-dichloro- and 2,2-dibromovinyl)-phosphoric acid ester, O,O-diethyl-O-(4-nitro-phenyl)-thionophosphoric acid ester, O,O-dimethyl-O-(3-methyl-4-methylthio-phenyl)-thionophosphoric acid ester, O,O-dimethyl-O-(3-methyl-4-nitro-phenyl)-thionophosphoric acid ester, O-ethyl-S-n-propyl-O-(2,4-dichlorophenyl)-thionophosphoric acid ester, O-ethyl-S-n-propyl-O-(4-methylthio-phenyl)-thionophosphoric acid ester, O,O-dimethyl-S-(4-oxo-1,2,3-benzotriazin-3-yl-methyl)-thionophosphoric acid ester.

O-methyl-O-(2-iso-propyl-6-methoxy-pyrimidin-4-yl)-thionomethanephosphonic acid ester, O-O-diethyl-O-(2-iso-propyl-6-methyl-pyrimidin-4-yl)-thionophosphoric acid ester, O,O-diethyl-O-(3-chloro-4-methyl-coumarin-7-yl)-thionophosphoric acid ester, O,O-dimethyl-2,2,2-trichloro-1-hydroxy-ethane-phosphonic acid ester, O,O-dimethyl-S-(methylaminocarbonyl-methyl)-thionophosphonic acid ester, O-O-methyl-O-(6-methoxy-2-tert-butyl-pyrimidin-4-yl)-thionoethanephosphonic acid diester.

10. The method according to claim 6, wherein the insecticide is

N-methylcarbamic acid esters: 2-methyl-phenyl, 2-ethyl-phenyl, 2-iso-propyl-phenyl, 2-sec-butyl-phenyl, 2-methoxy-phenyl, 2-ethoxy-phenyl, 2-iso-propoxy-phenyl, 4-methyl-phenyl, 4-ethyl-phenyl, 4-n-propyl-phenyl, 4-methoxy-phenyl, 4-ethoxy-phenyl, 4-n-propoxy-phenyl, 3,4,5-trimethyl-phenyl, 3,5-dimethyl-4-methylthio-phenyl, 3-methyl-4-dimethylaminophenyl, 2-ethylthiomethyl-phenyl, 1-naphthyl, 2,3-dihydro-2,2-dimethyl- 7-benzofuranyl, 2,3-(dimethylmethylenedioxy)-phenyl, 2-(4,5-dimethyl-1,3-dioxolan-1-yl)-phenyl, 1-methylthio-ethylideneamino, 2-methylthio-2-methylpropylideneamino and 1-(2-cyano-ethylthio)-ethyllideneamino.

* * * * *

UNITED STATES PATENT AND TRADEMARK OFFICE
CERTIFICATE OF CORRECTION

PATENT NO. : 5,741,501
DATED      : April 21, 1998
INVENTOR(S): Jutus, et al.

It is certified that error appears in the above-indentified patent and that said Letters Patent is hereby corrected as shown below:

Col. 13, Next to last line     Delete " O-O-methyl-O- " and substitute -- O-methyl-O- --

Signed and Sealed this

Twenty-fourth Day of November,1998

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,741,501
DATED : April 21, 1998
INVENTOR(S) : Karl Justus et al.

It is certified that error appears in the above-identified patent and that said Letters Patent is hereby corrected as shown below:

Column 12,
Lines 25-40, the formula should read:

--

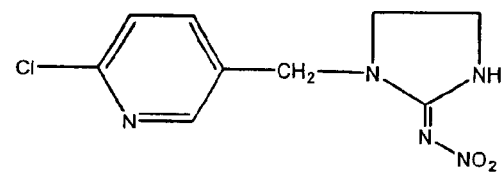

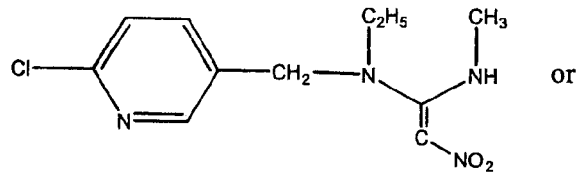 or

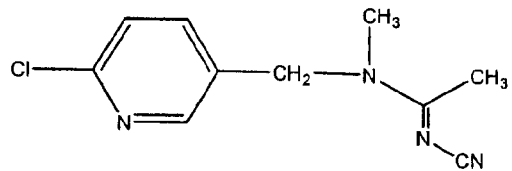

--

Signed and Sealed this

Seventeenth Day of February, 2004

JON W. DUDAS
*Acting Director of the United States Patent and Trademark Office*